(12) United States Patent
Zik

(10) Patent No.: US 6,191,151 B1
(45) Date of Patent: Feb. 20, 2001

(54) THERAPY FOR HERPES NEUROLOGICAL VIRAL CONDITIONS UTILIZING 1,4-DIHYDROPYRIDINE CALCIUM CHANNEL BLOCKERS

(76) Inventor: Howard M. Zik, 3169 Gomer St., Yorktown Heights, NY (US) 10598

( * ) Notice: Under 35 U.S.C. 154(b), the term of this patent shall be extended for 0 days.

(21) Appl. No.: 09/190,400

(22) Filed: Nov. 11, 1998

Related U.S. Application Data

(60) Provisional application No. 60/065,145, filed on Nov. 12, 1997.

(51) Int. Cl.[7] .......................... A61K 31/44; A61K 31/52

(52) U.S. Cl. ............................................ 514/356; 514/262

(58) Field of Search ..................................... 514/356, 262

(56) References Cited

U.S. PATENT DOCUMENTS 4,663,317 * 5/1987 Albrecht et al. ..................... 514/211

OTHER PUBLICATIONS

Fujibayashi et al, Embase Abstracts Online, abstract No. 87193585, 1987.*
The Nature of Bell's Palsy, Jerome A. Hilger, M.D., St. Paul, Mn., pp. 228–235, Jan. 25, 1949.
The Possible Role of Vascular Changes in the Aetiology of Bell'Palsy, Michael J. Blunt, Dept. of Anatomy, St. Bartholomew's Hospital Medical College, pp. 701–713, 1957.
On The Pathogenesis of Bell's Palsy, U. Fisch and H. Felix, ENT–Dept. of the University of Zurich, Zurich, Switzerland, Acta Otolaryngol 95:532–538, 1983.
Plasma Endothelin Level in the Acute Stage of Bell Palsy, Minoru Ikeda, MD; Masamichi Iijima, MD; Nobuo Kukimoto, MD; Mutsumi Kuga, MD, Arch Otolargyngol Head Surg/vol. 122, Aug. 1996, pp. 849–852.
Bell's Palsy Treatment With Acyclovir and Prednisone Compared With Prednisone Alone: A Double–Blind, Randomized, Controlled Trial, John M. Ruboyianes, MD; Christopher S. Trent, MD et al.; Cranial Nerve Research Clinic, Dept. of Head and Neck, Ann Otol Rhino: Laryngo:105:995, pp. 371–377, 1996.
Reactive Astrocytes In Viral Infections of the Human Brain Express Endothelin–like Immunoreactivity; Kuo–Chun Ma, Xiao Jing Nie, et al., Journal of the Neurological Sciences 126 (1994), pp. 184–192.
Cranial Polyneuritis and Bell Palsy, Adour KK, Arch Otolaryngol, May 1976, 102(5), pp. 262–264, abstract only.
Facial nerve paralysis induced by herpes simple virus in mice: an animal model of acute and transient facial paralysis; Sugita, T.; Murakami S.; Yanagihara N.; Fujiwara Y.; Hirata Y.; Kurata T.; Dept. of Otolaryngology Ehime Univ. School of Medicine, Japan, Ann Otol Rhinol Laryngol, 1995 Jul., 104(7): pp. 574–581, abstract only.
Ramsay Hunt facial paralysis: clinical analyses of 185 patients, Robillard R.B., Hilsinger R.L., Jr., Adour K.K., Otolaryngol Head Neck Surg., Oct. 1986; 95(3Pt 1), pp. 292–297, abstract only.

Molecular temporal bone pathology: IV. Analysis of DNA template length using mitochondrial PCR primers, Wackym, P.A., Kerner M.M., Grody, W.W., Laryngoscope, Aug. 1998; 108(8 Pt 2 Su 88); pp. 4–7, abstract only.
Treatment of Ramsay Hunt syndrome with acyclovir–prednisone: significance of early diagnosis and treatment, Murakami S., Hato, N., Horiuchi J., Honda N., Gyo K., Yanagihara N.; Ann Neural, Mar. 1997; 41(3), pp. 353–357, abstract only.
Identification of new protein kinase–related genes in three herpesviruses, herpes simplex virus, varicella–zoster virus, and Epstein–Barr virus, Smith, R.F., Smith, T.F., J. Virol Jan. 1989: 63(1), pp. 450–455, abstract only.
Effects of felodipine, nifedipine and verapamil on cytosolic Ca2+ and contraction in vascular smooth muscle, Hagiwara, S., Mitsul M., Karaki H., Dept. of Veterinary Pharmacology, Faculty of Agriculture, Univ. of Tokyo, Japan, Eur J Pharmacol Mar 1993; 30;2341(1), pp. 1–7, abstract only.
Endothelin–1 significantly increased number of specific high–affinity 1,4–dihydropyridine (DHP) binding sites photolabelled on vascular smooth muscle cells with (–)–[3H]–azidopine, Drimal, J., Koprda V., Physiol Res 1996;45(1), pp. 51–58, abstract only.
Endothelin–induced vasoconstriction in man: variable modification caused by endothelium–derived relaxing factor, Sodium nirtropruside and calcium antagonists, Schweiz Med Wochenschr, Apr. 11, 1992; 122(15), pp. 559–562, abstract only.
Inhibition of herpes simplex virus replication by genistein, an inhibitor of protein–tyrosine kinase, Arch Virol 1993; 132(3–4); pp. 451–461, abstract only.
Thrombin receptor activatin stimulates astrocyte proliferation and reversal of stellation by distinct pathways: involvement of tyrosine phosphorylation, Grabham, P., Cunningham, D.D., J. Neurochem 1995 Feb; 64(2), pp. 583–591, abstract only.

(List continued on next page.)

*Primary Examiner*—William R. A. Jarvis
(74) *Attorney, Agent, or Firm*—Gottlieb, Rackman & Reisman, P.C.

(57) ABSTRACT

A therapy for Bells Palsy in mammals is proposed that rests on a causal hypothesis involving both endothelin and the herpes virus, particularly the herpes simplex virus for Bell's Palsy. Similarly, the same therapy would apply to Ramsay Hunt, but in this case the herpes zoster virus would be involved in the causal hypothesis. Other herpes viral related conditions are also suggested to be amenable such as herpes simplex encephalitis. The therapy uses therapeutically effective doses of calcium channel blockers that are of the 1,4-dihydropyridine derivative class, such as felodipine but also including nifedidine, nimodipine, nisodipine or alenodipine. The treatment is proposed as continuing up to the tenth day of progression, but to be started as early as possible. Acyclovir or other herpes antagonists such as famciclovir may also be administered in therapeutically effective dosages.

47 Claims, 2 Drawing Sheets

OTHER PUBLICATIONS

Effects of felodipine on microvascular resting tone and responses to nerve stimulation and perfusion pressure reduction in rabbit skeletal muscle, Lindbom, L., Persson, M.G., Ohlen A., Borgstrom P., Gustafsson, D., J. Cardiovasc Pharmacol 1990 Apr.; 15(4), pp. 592–597, abstract only.

Spatial occupancy of vessels andfacial nerve in the facial canal, Ogawa, A., Sando I., Ann Otol Rhinol Laryngol, Jan.–Feb., 1982;91 (1 Pt 1): 14–9, abstract only.

Plendil (Felodipine) Extended–Release Tablets; Physicians' Desk Reference, 1998, pp. 526–528.

ADAL Capsules (Nifedipine), Physicians' Desk Reference, 1998, pp. 600–603.

* cited by examiner

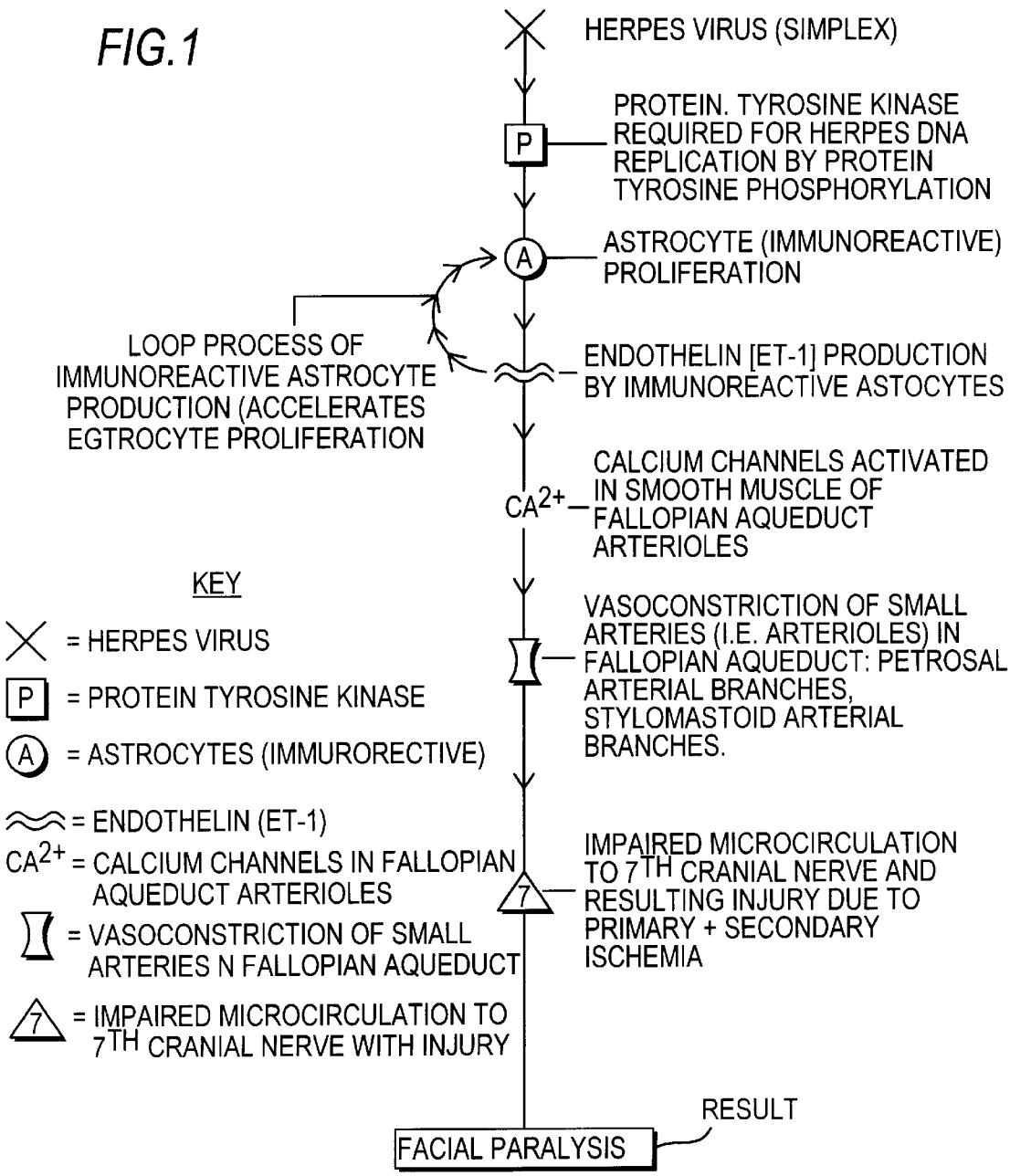

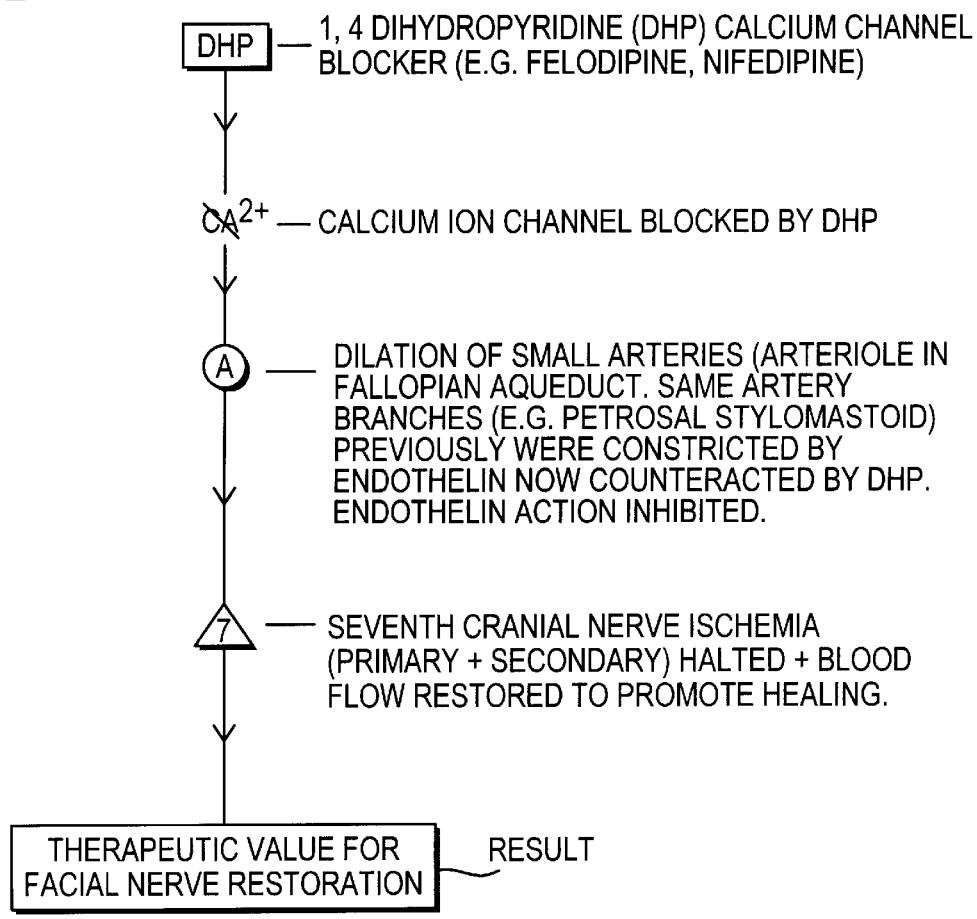

THERAPY FOR HERPES NEUROLOGICAL VIRAL CONDITIONS UTILIZING 1,4-DIHYDROPYRIDINE CALCIUM CHANNEL BLOCKERS

This patent claims priority of Provisional Application No. 60/065,145 filed Nov. 12, 1997.

FIELD OF THE INVENTION

The present invention relates to the treatment of certain herpes viral neurological conditions in mammals, principally Bell's Palsy, a palsy of the facial nerves, and to the use of calcium channel blockers coupled preferably with a herpes virus antagonist in a treatment therapy. Other herpes conditions include Ramsay Hunt and other herpes caused neurological conditions such as Herpes Simplex Encephalitis.

BACKGROUND OF THE INVENTION

Bell's Palsy (originally described by Charles Bell, 1812) is recognized as a palsy of the facial nerve, generally the seventh cranial nerve. It most commonly affects one side of the face, may be partial or total, and has a progression time of 7 to 10 days. Regarded in the past as idiopathic, there has recently been convincing evidence that it has its cause in the herpes type virus of the simplex type. Some physicians reassure patients that the disease will most likely remit in a period lasting from 3 weeks up to 6 months, (leading some physicians to advocate a no action policy other than facial management, sometimes referred to as "therapeutic nihilism") but the fact remains that about 24% of the victims with current popular therapies are left with some residual paralysis or other aftereffects such as hemi-facial spasm, synkinesis, or loss of tearing or blinking capacity.

An understanding as to the likely physiological events (without an identification of their cause) was comprehensively put forward by Hilger (Hilger J, *The Nature of Bell's Palsy. Laryngoscope*, 54:228–235, 1949) and Blunt (Blunt M, *Possible Role of Vascular Changes in the Etiology of Bell's Palsy, J. Laryngol Otol,* 70:701–713, 1956)) where they maintained that vasoconstriction of the arterioles within the fallopian aqueduct of the temporal bone was responsible for the facial palsy. This vasoconstriction was believed to lead to primary ischemia (tissue anemia) entailing edema of the nerve sheath and a secondary ischemia due to nerve compression. K. Adour opposed this account and instead put forward a viral theory (Adour K K, *Cranial Polyneuritus and Bell's Palsy, Arch Otolarygol,* 102:262–4, 1976) based on herpes simplex reactivation and maintained that Bell's Palsy was polycranial which was believed to be inconsistent with an ischemia scenario. However, support of the former ischemia outlook was provided through anatomical electromyographical and histopathological studies summarized by U. Fisch (Fisch U. and Felix, H, *On the Parthenogenesis of Bell's Palsy. Acta Otolaryngol,* 95:532–538, 1983)). Further the ischemia description of events fits well with later causal analysis by M. Ikeda (Ikeda M et al, *Plasma Endothelin Level in the Acute Stage of Bell Palsy, Arch Otolyaryngol Head Neck Surg,* 122:849–852, August 1996) involving endothelin findings; and work on the immunological role of endothelin has been inferentially linked by the inventor to an ischemia scenario (which requires—a herpes viral role) as will be later explained.

Current therapy mainly involves the administration of steroids, particularly prednisone (see U.S. Pat. No. 2,897, 216) within the first 3 days of onset, where the standard initial prednisone dosage is about 30 mg. and is tapered off over a 5 day period to a 10 mg. level. In parts of Japan and Europe the steroid treatment has taken the form of heavier steroid dosages, mainly cortisone, incorporated within an IV infusion of low molecular dextran (Kinishi M et al., *Conservative Treatment of Hunt Syndrome, Nippon Jibinkoka Gakkai Kaiho,* 95:1, 65–70, 1992) (See U.S. Pat. No. 2,841,578). The theory underlying steroid treatment, either by prednisone or the higher dosage method, is to improve microcirculation, which has been impaired due to inflammation affecting the seventh cranial nerve. It may be noted that steroid treatment of the high dosage type has its share of hazards that leave many physicians uncomfortable, and which includes serious hepatic and renal disorders.

Recently a new element of approach that is coupled with steroid therapy has emerged from the work of Dr. Kedar Adour, who for many years had maintained that the herpes simplex virus is the original causal agent in Bell's Palsy. Based on this belief, Adour has advocated the use of acyclovir (See U.S. Pat. No. 2,539,963) (commonly used for treating herpes viral infections) for treating Bell's Palsy. He has in this effort conducted a double blind study (Adour K K et al., *Bell's Palsy Treatment With Acyclovir And Prednisone Compared With Prednisone Alone: A Double-Blind, Randomized Controlled Trial. Otol Rhinol. Larygnol* 1996;105:371–378.) (Kaiser Permanente Medical Center), which provides viable support for the use of acyclovir, an established herpes virus inhibitor. The study compared an acyclovir-prednisone group of subjects with a prednisone-placebo group and the following results were obtained: a 92% volitional motion recovery rate for the acyclovir group versus 76% for the prednisone-placebo group, and an 87% prevention rate of nerve degeneration for acyclovir-prednisone versus 70% for prednisone-placebo. Although the number of subjects was one hundred, about equally split in the 2 groups, results are both statistically significant and in agreement with other studies supporting a herpes simplex or herpes family origins of Bell's Palsy. These studies include the work of Sugita (Sugita T et al, *Facial Nerve Paralysis Induced by Herpes Simplex Virus in Mice: An Animal Model of Acute Transient Facial Paralysis, Ann Otol Rhinol Laryngol* 104(7):574–581, July 1995) inducing apparent Bell's Palsy in mice with herpes simplex and the work of Murakami, pointing chiefly to herpes simplex but sometimes invoking other herpes viruses.

Further, recently there has been a significant study by M. Ikeda (Nihon University School of Medicine, Tokyo Japan) linking endothelin, a peptide of 21 amino acids with Bell's Palsy. This study is yet to receive sufficient attention, however it sheds important light on some of the immediate causal events underlying Bell's Palsy. Endothelin is an extremely potent constrictor of blood vessels, particularly smaller ones, and Ikeda maintains that impairment of microcirculation through primary and secondary ischemia in the fallopian aqueduct (and thereby drawing on the earlier work of Hilger and Blunt) is responsible, but what is new here is the role of endothelin in bringing this about. Ikeda, however, regards the etiology of Bell's Palsy as unknown or idiopathic, and does not offer any causal hypotheses for the high endothelin levels.

There are some other current therapies in addition to steroids, but they do not enjoy a similar popularity, although they are occasionally used in conjunction with it. This includes surgical decompression, more prevalent in previous decades, beginning in the thirties, although sometimes still employed (Jabor M A, *Management of Bell's Palsy, J LA State Medical Soc,* 146(7): 279–283, 1996) where damage is assessed as extensive. Additionally included is electrical stimulation (also used in previous decades (Devrese P P et al., *Electrotherapy in Facial Paralysis, ORL Otorhinolarygol Relat Spec,* 1974; 36(2): 94–99) acupuncture and biofeedback (May M, et al, *Bell's Palsy: Management of Sequelae Using EMG. Rehabilitation, Bottulinum and Surgery, Am J Otol,* 10(3):220–229, May 1989)). There appears to be no conclusive studies on these techniques and anecdotal evidence is at best mixed. As for surgery, it has its special hazards, while being based upon the ischemia hypothesis.

In addition to the discussed therapies designed to alleviate or minimize damage, management approaches including eye patches and artificial tears are almost invariably offered to avoid permanent eye damage. Electrical conductivity tests are also used and are of significant value in assessing permanent nerve damage of degeneration. Facial massage is sometimes also recommended to aid in circulation and avoid atrophy once muscle movement returns.

There have been 4 patents (U.S. Pat. Nos. 5,589,183, 5,542,437, 5,148,477, 4,817,628) since 1971 that deal with Bell's Palsy. Of the four, two deal with facial management by mechanical devices, and two are electrically diagnostic for assessment purposes.

Ramsay Hunt syndrome (also known as "herpes zoster oticus") is also caused by a herpes virus, but in this case the herpes zoster virus, as was maintained (the condition) by J. Ramsay Hunt in 1907. Ramsay Hunt syndrome frequently results in facial paralysis involving the seventh cranial nerve (as with Bell's Palsy) but also commonly affects other cranial nerves including the 5th 9th and 10th and 11th). (Further, it should be noted that Ramsay Hunt syndrome as referred to in this invention is Ramsay Hunt Type I, not to be confused with Ramsay Hunt Type II, an entirely different condition which is a rare degenerative neurological disorder characterized by epileptic type fits and myoclonus.) Ramsay Hunt is often accompanied at onset by auricular vesicles, sometimes also found on face, neck or scalp and frequently results in hearing loss (48.2% according to S. Murakami). (Murakami S. et al., *Clinical features and Prognosis of Facial Palsy and Hearing Loss in Patients With Ramsay Hunt, Nippon Jibiinkoka Gakkao,* 99:12, 1772–1779, December 1996) Intense ear pain and vertigo and tinnitus are also common manifestations. Ramsay Hunt in relation to facial paralysis of the seventh cranial nerve (as with Bell's palsy) is found to have a less favorable recovery profile than the latter (Robillard R B et al., *Ramsay Hunt Facial Paralysis: "Clinical Analysis of* 185 *Patients, Otolaryngol Head Neck Surg,* 95 (3pt1):292–297, October 1986) Complete recovery rates are estimated at about 52% (Murakami S. *Nippon Jibiinkoka Gakkai Kaiho, December* 1996 99:12, 1772–9) compared with 76% of Bell's palsy.

In conjunction with the early theory of J. Ramsay, the presence of herpes zoster varicella virus has been confirmed more recently in patients having Ramsay Hunt according to studies by Robillard (Robillard R B et al. *Otolaryngol Head Neck Surgery:*292–297, October 1986) and Wackym (Wackym, P A, *Molecular Temporal Bone Pathology: II Ramsay hunt Syndrome, Laryngoscope,* 1997; 107:9 1165–75, September 1997). In Wackmyn's study the DNA was confirmed in the temporal bone sections in the geniculate ganglia thereby strongly supporting the hypothesis put forth by Ramsay, and which revealingly is within the areas of the temporal bone that Hilger and Blunt maintained are affected in Bell's palsy namely the petrosal and stylomastoid arteries. In recent years the use of acyclovir has been used often in combination with prednisone (Murakami, S et al., *Treatment of Ramsay Hunt Syndrome with Acyclovir Prednisone, Significance of Early diagnosis and Treatment, Ann. Neuro;* 41(3): 353–357, March 1997) in order to treat Ramsay Hunt, paralleling this current treatment of Bell's palsy. Steroid therapy has also been applied (Adour K K and Hetzler D G, *Current Treatment for Facial Palsy, Am J Otol,* 5(6):499–502, October 1984) as well as the use of other therapies discussed for Bell's Palsy i.e. surgical decompression and electrical stimulation. As with Bell's palsy, there is no conclusive studies on these techniques and anecdotal evidence is at best mixed for this more severe condition. Eye patch treatments due to loss of blinking reflex have been incorporated as in Bell's palsy. Further with regard to the vertigo of Ramsay Hunt, diazepam has been utilized to control this symptom. In summation there is a clear overlap of Ramsay Hunt with Bell's Palsy with regard to past theory and proposed treatment.

BRIEF DESCRIPTION OF THE INVENTION

The present invention is directed to the alleviating the effects of Bells Palsy and Ramsay Hunt as well as other herpes caused neurological conditions by providing a therapy that directly addresses the mechanisms believed to cause the ailment. The invention was realized by an analysis of the existing medical literature on the disease and by developing what the inventor believes to be a novel coherent perspective identifying the most significant causation factors and by determining a pharmacology directed to affecting those factors. Thus, although the invention has been achieved without experimentation on humans, it represents the results of an analysis of medical and pharmacological considerations not previously reported for the treatment of a very serious and debilitating ailment. Although logically arrived at, the invention is not the result of merely following markers laying out the path to its discovery in the existing literature.

The therapy disclosed in this application will rest on a proposed causal hypothesis involving both endothelin and herpes simplex virus for Bell's palsy and other herpes virus for other conditions (e.g. herpes zoster for Ramsay Hunt). Calcium channel blockers that are of the 1,4-dihydropyridine derivative class, especially felodipine but also including nifedidine, nimodipine (See U.S. Pat. No. 3,799,934), nisoldipine (See U.S. Pat. No. 4,154,839) or alenodipine may be utilized to treat Bell's Palsy and other herpes causing neurological conditions. The treatment is proposed as continuing up to the tenth day of progression, but to be started as early as possible. The treatment is based on a proposed dynamic for the pathological process underlying Bell's Palsy and the other conditions. The proposed therapy is designed to counter the effects of this pathological process as well as inhibit the very process itself. In a further embodiment, acyclovir, a herpes virus antagonist that can stem herpes viral DNA replication may be used in support of the DHP treatment.

The pathological process supported is the pathological process described by Hilger and Blunt in which vasoconstriction of arterioles in the fallopian aqueduct of the temporal bone; however, it is here suggested that this process is itself brought about by an immunoreactive response to a herpes virus, mainly the herpes simplex virus. This response entails the production of the peptide endothelin, one of the most potent natural vasoconstrictors known. Endothelin achieves its vasoconstriction through the release of calcium ions (CA2+) into the smooth muscle tissue of arteries, particularly the smaller arteries (arterioles). The vasoconstriction which results impairs microcirculation to the facial nerve (seventh cranial nerve) by primary and secondary ischemia.

The use of DHP calcium channel blockers, particularly felodipine, nifedipine, nimodipine, or nisodipine should result in (1) rapid vasodilation of the aqueduct arterioles (2) reduced resistance in the arterioles (3) the blocking of the same channel through which endothelin acts and therefore functionally impairing endothelin's mechanism for generating vasoconstriction. Adequate circulation should then follow with blood and oxygen flow to the seventh cranial nerve. The restoration of adequate microcirculation should then avert further damage and allow immediate blood flow to promote healing. This treatment should compare favorably to current popular steroid approach in that it precisely targets the pathological process, rather than deploying a general anti-inflammatory agent to achieve dilation. Steroid use should only be effective to the extent it counters the effects of a high endothelin level, which it does only indirectly as an anti-inflammatory agent. Felodipine is particularly suited for a more direct and effective role since in comparison studies with other DHP calcium channel blockers in treating hypertension it is more effective in its arterial action. Moreover, it has been shown to effect arterioles of the order of size found by arterioles in the fallopian aqueducts. Further, it is designed to selectively effect smooth muscle as opposed to cardiac and smooth muscle (nifedipine) which is the main component of the smaller arteries (i.e. arterioles) which comprise the fallopian aqueduct. Additionally, prednisone as well as other steroids contain various known hazards including hepatic and renal disorders. The steroids are also immunosuppressive agents and inhibit processes needed for combating any herpes infection. Moreover, in contrast to other proposed therapies such as electrical stimulation and biofeedback, the DHP calcium channel blocker therapy is based on a consideration of a viable understanding of the Bell's Palsy pathological process and its dynamics. Surgery also has various hazards with limited success and has consequently diminished in use over recent years.

The same dynamics and treatment regimen involving 1,4 DHP Dihydorpyridine calcium channel blockers proposed here for Bell's Palsy would also lend itself to treatment of Ramsay Hunt. The vasoconstriction of arterioles in the fallopian aqueduct would result in primary and secondary ischemia with all the mentioned microcirculatory problems in both conditions, although in Ramsay Hunt the herpes zoster virus rather than the herpes simplex is the initiating causal factor. However, the same 1,4-dihydopyridine calcium channel blockers should counter and inhibit the pathological process in light of the parallel vasoconstriction of the same arterioles mentioned previously for the studies by P. Wackmyn and R B Robillard. Further, there is some evidence that endothelin (ET-1) can be specifically linked to an immunological reaction to the herpes zoster virus and other herpes virus (Smith R F and Smith T F, *Identification of New Protein Kinase in Three Herpes Viruses, J Virol,* 63:1, 450–455, January 1989) and also involve astrocytes (*Kuo-Chun Ma et al., Reactive astrocytes in Viral Infections of the Human Brain Express Endothelin-Like Immununeoactivity, J Neurol Sci,* 126, 184–192, *November* 1994) as vital agents in the process.

Similarly the invention strongly suggests other herpes viral conditions such as herpes simplex encephalitis may be similarly treated insofar as similar viruses, vasoconstriction, endothelin and astrocytes (Kuo-chun Ma) may be involved.

BRIEF DESCRIPTION OF THE DRAWINGS

FIG. 1 is a schematic of process of Bell's Palsy Pathological Progression and may also serve as a model for other herpes causing neurological conditions e.g. Ramsay Hunt.

FIG. 2 is a schematic of the proposed therapy of Bell's Palsy with DHP Calcium Channel Blockers, and a model for the other herpes causing neurological conditions e.g. Ramsay Hunt.

DETAILED DESCRIPTION OF PREFERRED EMBODIMENTS

The proposed therapy should be administered as soon as possible upon the first diagnosis of Bell's Palsy or other herpes causing neurological conditions and continue up to the tenth day after first symptoms. Damage as mentioned may be regarded as being brought about by primary and secondary ischemia originating in vasoconstriction of blood vessels in the fallopian aqueduct; consequently, the earlier that microcirculation to the seventh cranial nerve may be restored within the aqueduct, the sooner further damage could be averted as well as natural healing processes activated. The vasoconstriction brought about by endothelin action may involve such arteries and their branches as the petrosal artery branches (Fisch U. and Felix H., *On the Parthenogenesis of Bell's Palsy, Acta Otolaryngol,* 95:532–538, May 1983; Blunt M, J. *Laryngol Otol,* 70:701–713, 1956 and stylomastoid artery (Blunt M. J. *Laryngol Otol.,* 1956); Hilger J, *Laryngoscope.,* 54:228–235, 1949). DHP calcium channel blockers are preferred for their vasodilatory capacity and in the reduced peripheral resistance that they offer to blood flow, resulting from their blocking action of calcium ions channels, the very channels stimulated by endothelin to produce calcium ions.

A preferred embodiment is to use felodipine, which is selective to smooth vascular muscle tissue, the very tissue comprising the arterioles (composed mainly of smooth muscle tissue) the vessels most effected in the vasoconstriction of Bell's Palsy. Due to felodipine's selectivity and other characteristics felodipine is especially suited as a promising Bell's Palsy treatment agent. These characteristics include its effect on smaller arterioles of the magnitude found in the fallopian artery networks, as well as its consistent superior effectiveness (Hagiwara S et al., *Effects of Felodipine, Nifedipine and Verapamil on Cystolic Ca2+ on Contraction of Smooth Muscle Tissue, Eur Journal Pharmacol,* 234(1):1–7, March 1983) in vasodilation found in blood pressure reduction by felodipine compared with nifedipine. The blood brain barrier which may limit the effectiveness in reaching these arteries (although somewhat borderline in their location) is also penetrated rather well by felodipine as clinically supported.

Another embodiment of the present invention is to employ nifedipine, which has been proven effective against angina for relief of spasm of arteries or arterioles as well as being selective to both coronary and smooth muscle.

Nisodipine, another DHP calcium channel blocker acting on the same sites is effective in much lower dosage levels than felodipine and also avoids the coronary areas.

Nimodipine, a dihydropyridine (DHP) used to treat SAG hemorrhaging is most effective in this latter capacity. Further, it may be noted that tests in countering the effects of endothelin were primarily done with respect to nifedipine (Kiowaski W. et al., *Endothelin-induced Vasoconstriction in Man; Variable Modification caused by endothelium-Derived Relaxing Factor, Schweiz Med Worchenschr,* 122:15:559–562, April 1992; Meyer, P et al., *Effects of Calcium Channel Blockers on the Response to Endothelin-*1, *Bradykinin and Sodium Nitroprusside in Porcine Ciliary Arteries., Exp Eye Res,* 60:5: 505–10, May 1995) Significantly, however, there is a 1996 study (Drimal J. and Koprda V., *Endothelin 1 Significantly Increased Number of 1,4-Dihydropyridine Binding Sites Photolabelled on Vascular Smooth Muscle Cells with (−) {3H}-Azidopine, Physiol Res,* 45(1):51–58, 1996) which shows binding sites for endothelin have a high affinity for DHP calcium channels and hence the DHP calcium channel blockers as a group may share this advantage.

As mentioned earlier, Hilger in the 1940's and Blunt in the 1950's offered a physiological account of the destructive vascular process involved in Bell's Palsy. This process, although viable and accepted by some, but challenged by Adour, can now be seen as compatible and supported by the endothelin studies conducted by M. Ikeda (Ikeda M. et al., *Plasma Endothelin Level in the Acute Stage of Bell's Palsy, Arch Otolaryngol Head Neck Surg,* 122:849–852, August 1996). These endothelin studies, moreover, when considered along side other studies on endothelin (involving immunological mechanisms) as well as recent herpes virus findings can now be seen as supporting the coherent picture of a Bell's Palsy dynamic developed by the inventor, and one that warrants in the opinion of this inventor the use of DHP channel blockers as a high powered therapy. Consequently, the inventor believes it is appropriate to implement a therapy based upon a first causal agency (herpes virus) and related underlying process involving endothelin (intermediate causal agency) for the physiological events described in Hilger and Blunt. Ironically, the process involved is in agreement with a herpes viral action, but an action that Adour mistakenly construed as inconsistent with an ischemia account in rejecting the latter.

FIGS. 1 and 2 schematically represent the relevant process and therapy.

There is good indication that herpes virus infection results in the creation of protein tyrosine kinase needed for herpes viral replication (Yura, Y et al, *Inhibition of Herpes Simplex Virus Replication by Genestein, an Inhibitor of Protein Tyrosine Kinase, Arch Virol,* 132:3–4:451–461, March 1993). Moreover, there is convincing evidence (Grabham P. and Cunningham D D, *Thrombin Receptor Activation Stimulates Astrocype Proliferation and Reversal of Stellation by Distinct Pathways: involvement of Tyrosine for Phosphorylation, J Neurochem,* 64:2:583–91, February 1995) and (Stanmirouvic D B, *The role of Intercellular Calcium and protein Kinase in Endothelin stimulated Proliferation of rat type I Astrocytes, Glia,* 15:2, 119–130, October 1995) that protein tyrosine kinase needed for herpes replication is basically involved in stimulating an immunological reaction for astrocyte cell production. Astrocytes are one of the basic cells found in certain tissues of the peripheral nervous system. Further, proliferation of immunoreactive astrocytes in the brain has been shown to result in endothelin production (ET-1) (K. Ma), and has been traced in 5 out of 9 cases examined by Ma to be stimulated by confirmed herpes simplex inflammatory infections. Endothelin, moreover is a known mitogen, and as such leads to multiple astrocyte cell production. This entails a kind of loop or reciprocal effect whereby endothelin and astrocytes synergistically produce heightened endothelin and astrocyte levels. Endothelin, as mentioned, specifically ET-1 is an extremely potent vasoconstricting agent and achieves its vasoconstricting effects by precisely stimulating those calcium channels sites through which DHP calcium channel blockers act. (Hayes, Drimal). Therefore, the DHP calcium channel blockers impair the process of vasoconstriction itself while by appropriate dosage management may even achieve vasodilation beyond simply countering the effects of endothelin.

Felodipine's effect on reversing the contractile process and replacing it with dilation and reduced blood resistance is selective with respect to vascular smooth muscle with little or no effect on cardiac muscle. Further, felodipine can penetrate the blood brain barrier to the extent that this barrier may be a problem for effective contact with arteries.

Nimodipine is also selective and is particularly selective for cerebral arteries, but clinical tests on other aspects of its effectiveness such as dilation and reduced resistance of smaller arteries is not as extensive. Nimodipine may, however, be considered especially relevant to potentially treating herpes simplex encephalitis insofar as this disease involves herpes infection of the inner brain regions of the cerebral cortex. The responding endothelin immunoreactivity in this region (*Kuo-chun Ma et al., J. of Neurological Sciences* 126:184–192, June 1994) also lends it to the felodipine and nifedipine approaches.

Nisodipine is more potent and long lasting per unit dosage than nifedipine and in contrast is selective with respect to countering the contractile effects of vascular smooth muscle as opposed to cardiac muscle. It has, furthermore, been used effectively in treating hypertension The effect of felodipine on arterioles of even smaller magnitude than the fallopian arterioles has been experimentally supported Lindbom L et al, *Effects of Felodipine on Microvascular Resting Tone and Responses to Nerve Stimulation and Perfusion Pressure Reduction in Rabbit Skeletal Muscle, J Cardiovasec Pharmacol:* 15(4), 592–597, April 1990). Arterioles in the fallopian aqueduct are in a range of 25 to 76 microns (Ogawa A and Sando I, *Spacial Occupancy of Vessels and Facial Nerve in Facial Canal . Ann OtolRhinol Laryngol,* 91:14–19, 1982. Endothelin has been shown to constrict arterioles of this magnitude (Kuo, K C et al. *Effects of Endothelin-1 on skeletal Muscle Microcirculation, Microcirculation Annual:* 1992:45–46). Felodipine has been shown in the Lindbom experiments (Lindbom L et. al. *J. Cardiacvasec Pharmacol,* 14(4):593–597, April 1990) to dilate arterioles of an even smaller magnitude: 10–20 microns of the transverse type and 4–8 microns of the terminal type. Felodipine is known to result in vasodilation of arterioles at oral levels between 2.5 and 20 mg once daily for extended release tablets in treatment of hypertension, and which represents the dosage range proposed in this invention for Bell's Palsy and Ramsay Hunt; a daily dosage of 10 mg. appears to be most effective per dosage unit in dealing with hypertension and represents the preferred level in this invention for Bell's Palsy and Ramsay Hunt. However, it should be noted that a greater consideration may be given to the higher end of this range (e.g. 15 mg) for Ramsay Hunt in light of its greater neurological severity. Following oral administration, it is almost completely absorbed and obtains peak levels in 2–5.5 hours. In its treatment of hypertension, a daily administration is sufficient to manage the condition and this would seem a good practical guide in addressing Bell's Palsy and Ramsay Hunt.

If nifedipine is used, peak levels are reached in 30 minutes at dosage levels of 10 mg. as a preferred level for immediate release tablets and dosage ranges of 10–20 mg. may be administered 3 times daily for effective treatment for Bell's Palsy and Ramsay Hunt, or once daily for extended release tablets at dosage level of 30–60 mg. with preferred level at 30 mg. These proposed dosage levels and ranges track with effective treatment of hypertension and angina, and are associated with adequate vasodilation of arterioles.

Adverse effects for DHP calcium channel blockers are minimal with the most common being headaches (14.7% felodipine, 19% extended release 30 mg. nifedipine) for the group and mild peripheral edema (17%) for felodipine and occasional flushing (6.9% felodipine, 4% nifedipine) or dizziness (5.8% felodipine, 4% nifedipine). To the extent the DHP group is used for treating hypertension, blood pressure may drop where averaging for felodipine at 10 mg. dosage level is 5.3/7.2 systolic and 2.7/2.5 diastolic over a 4 week period for individuals treated. The average reduction over a 6 week period for nifedipine at 30 mg was 5.5/2.9 (systolic/diastolic) and at 60 mg. was 8.0/4.1. Nimodipine as a preferred embodiment is recommended at a dosage of 60 mg. every 4 hours. This dosage tracks the standard dosage for subarachnoid hemorrhaging from ruptured congenital aneurysm, and recommended for effective treatment of that condition. There was a decrease in blood pressure in 4.4% of subjects reported in a study of 823 patients (Physicians Desk Reference 1998). It therefore avoids the common drop in blood pressure of the other DHP's. The most common adverse experience was nausea and rash (1.2% for each). Other adverse effects were below 1% and included hepatitis, itching and gastrointestinal itching. Its selectivity to smooth muscle as opposed to cardiac muscle (in poitive comparison with nifedipine) and its safe use in patients who are not suffering from hypertension renders it particularly attractive. Its success rate, however, compared to placebo groups was not especially great. Nisoldipine as an embodiment is an extended release DHP and the recommended daily dosage for treatment of Bell's palsy and Ramsay Hunt is 10–20 mg. per day. This tracks its treatment dosage for low to moderate hypertension. Adverse effects include mostly peripheral edema and headaches both at a 22% incidence rate. (pharyngitus-5%, sinusitis-2% ) The therapy for the DHP class may be avoided for individuals who are already hypotensive, or are sensitive to this class of channel blockers. There exists a potential hazard for the fetus of expecting mothers for this group based on some animal studies qualifying it as a class C drug in this area and such mothers should be so advised. Further the adjunct administration of acyclovir would be given in dosage of 2000 mg. daily (400 mg. 5 times daily) for 10 days (this was the K. Adour dosage in his acyclovir-prednisone study) as a means of inhibiting further viral action in setting off the endothelin production sequence. Alternatively 500 mg. of famciclovir taken every eight hours for seven days may be used.

Example of Treatment With DHP Calcium Channel Blockers

Treatment of Bell's Palsy or Ramsay Hunt with 1,4-dihydropyridine (DHP) calcium channel blockers is proposed with recommended administration beginning with the first signs and to continue up to the tenth day. Felodipine is likely to be particularly effective. The administration of DHP calcium channel blockers is based on a disease dynamic that begins with a herpes (simplex) viral invasion and ultimately leads to primary and secondary ischemia of the seventh cranial nerve in the fallopian aqueduct. The ischemia involves physiological events of a type described by Hilger and Blunt in the 1940's and 1950's, essentially entailing severe vasoconstriction of local arterial branches in the aqueduct area e.g. petrosal arterial branches. A key intermediary event is the production of endothelin (ET-1), unknown in earlier days, as a vasoconstrictive peptide through calcium ion action and generated as an immunoreactive by-product.

The use of 1,4-dihydropyridine (DHP) calcium channel blockers as one of the 5 classes of calcium channel blockers is proposed here as particularly tailored for treatment of Bell's Palsy as well as the other herpes causing neurological conditions (e.g. Ramsay Hunt) in light of its vasodilatory and resistance reduction properties, thereby counteracting and inhibiting the vasoconstrictive disease described above. The DHP group is especially suited to effect vascular smooth muscle by calcium channel blockage, where the smooth muscle is the main constituent of the small arteries i.e. the arterioles in the aqueduct region. The use of DHP has been proven effective in treating hypertension and angina. Felodipine would appear to be particularly efficient in treatment of Bell's Palsy because it is selective of smooth vascular muscle (without cardiac selectivity) as well as cerebral arteries, the very arterial elements involved, e.g. petrosal and stylomastoid. Further, it has been proven effective in dilating even smaller arteries than those imputed in Bell's Palsy and it can penetrate rather well the blood brain barrier. Also its consistency in dilation is superior. These facts make felodipine an especially suitable prospect for treatment. Nifedipine, however, is also promising insofar as it is the most experimentally proven in counteracting endothelin. Felodipine also enjoys such support, but to a lesser degree. Nimodipine is promising for its special effectiveness in blood brain barrier penetration and its relation to improved neurological condition by relief from ischemia in patients with subarachnoid hemorrhage from ruptured aneurysms. It has, furthermore, been used on safely for patients without hypertension and does not lower blood pressure significantly. Nisodipine enjoys unique long term unit dosage potency and remains selective to smooth vascular muscle. However, felodipine in this group appears especially suited to address the appropriate arteriole regions of Bell's Palsy and Ramsay Hunt and even herpes simplex encephalitus, although nimodipine is also well suited for the latter.

Appropriate dosage of felodipine based on treatment of vasoconstriction in hypertension would be of the order of 2.5 gm to 20 gm of extended release tablets daily for the 10 day progression period involved. Nifedipine could involve one 30–60 extended release tablet daily for a comparable period. Potential adverse effects are generally minimal, the most common being mild edema for felodipine, and dizziness or headaches for felodipine or nifedipine. The conjoint use of acyclovir as an adjunct to control viral replication would be 400 mg., 5 times daily for the 10 day period. The proposed utilization of DHP calcium channel blockers is designed to address the core of the pathological process of Bell's Palsy and thereby to halt and reverse its progression.

Although the invention has been proposed to be implemented by specific embodiments, there has been presented a broader understanding of the underlying dynamics justifying these embodiments. The invention therefore should not be limited exclusively to the described embodiments but should be determined from the interpretation of the following claims.

What is claimed is:

1. A method for the treatment of a patient having Bell's Palsy comprising dilating small arterioles in the patient's fallopian aqueduct to supply circulation to the 7th and other cranial nerve by administering to the patient therapeutically effective dosages of a 1,4 dihydropyridine calcium channel blocker.

2. A method for the treatment of a patient having Bell's Palsy comprising dilating small arterioles in the patient's fallopian aqueduct to supply circulation to the 7th and other cranial nerve by administering to the patient therapeutically effective dosages of a 1,4 dihydropyridine calcium channel blocker, wherein blood and oxygen flow to the seventh cranial nerve is enhanced.

3. The method of claim 2 wherein said calcium channel blocker is selected from the group consisting of felodipine, nifedipine, nimodipine, nisodipine and alenodipine.

4. The method of claim 2 wherein said calcium channel blocker is felodipine and said therapeutically effective dosage is sufficient to effect arterioles in the fallopian aqueducts.

5. The method of claim 2 wherein said calcium channel blocker is felodipine and said therapeutically effective dosage is a daily dose of between 2.5 and 20 mg.

6. The method of claim 2 wherein said calcium channel blocker is felodipine and said therapeutically effective dosage is a daily dose of 10 mg.

7. The method of claim 2 wherein said administration of the 1,4-dihydropyridine derivative calcium blocker continues for ten days.

8. The method of claim 2 further comprising the administration of therapeutically effective dosages of a herpes virus antagonist to stem herpes viral DNA replication.

9. The method of claim 3 wherein said calcium channel blocker is nisodipine administered at a dosage of 10–20 mg. per day.

10. The method of claim 3 wherein said calcium channel blocker is nimodipine administered at a dosage of 60 mg. every 4 hours.

11. The method of claim 3, wherein said felodipine is administered as extended release nifedipine in approximately a daily dose in the range of 30–60 mg.

12. The method of claim 3, wherein said felodipine is administered as extended release nifedipine in approximately a daily dose of 30 mg.

13. The method of claim 8 wherein said herpes virus antagonist is acyclovir or famciclovir.

14. A method for the treatment of a patient having Ramsay Hunt or other herpes neurological conditions comprising administering to the patient therapeutically effective dosages of a 1,4-dihydropyridine calcium channel blocker.

15. A method for the treatment of a patient having Ramsay Hunt or other herpes neurological condition comprising administering to the patient therapeutically effective dosages of a 1,4-dihydropyridine calcium channel blocker to enhance blood and oxygen flow to the seventh cranial nerve.

16. The method of claim 15 wherein said calcium channel blocker is selected from the group consisting of felodipine, nifedipine, nimodipine, nisodipine and alenodipine.

17. The method of claim 15 wherein said calcium channel blocker is felodipine and said therapeutically effective dosage is sufficient to effect arterioles in the fallopian aqueducts.

18. The method of claim 15 wherein said calcium channel blocker is felodipine and said therapeutically effective dosage is a daily dose of between 2.5 and 20 mg.

19. The method of claim 15 wherein said calcium channel blocker is felodipine and said therapeutically effective dosage is a daily dose of 10 mg.

20. The method of claim 15 wherein said administration of the 1,4-dihydropyridine derivative calcium channel blocker continues for ten days.

21. The method of claim 15 further comprising the administration of therapeutically effective dosages of a herpes virus antagonist to stem herpes viral DNA replication.

22. The method of claim 16 wherein said calcium channel blocker is nisodipine administered at a dosage of 10–20 mg. per day.

23. The method of claim 16 wherein said calcium channel blocker is nimodipine administered at a dosage of 60 mg. every 4 hours.

24. The method of claim 16, wherein said felodipine is administered as nifedipine in approximately a daily dose in the range of 30–60 mg.

25. The method of claim 16, wherein said felodipine is administered as nifedipine in approximately a daily dose of 30 mg.

26. The method of claim 21 wherein said herpes virus antagonist is acyclovir.

27. A method for enhancing blood circulation to the seventh cranial nerve comprising impairing endothelin's mechanism for generating vasoconstriction by the administration of a 1,4-dihydropyridine calcium channel blocker.

28. The method of claim 27 wherein said calcium channel blocker is selected from the group consisting of felodipine, nifedipine, nimodipine, and nisodipine.

29. The method of claim 27 wherein said calcium channel blocker is nisodipine administered at a dosage of 10–20 mg. per day.

30. The method of claim 27 wherein said calcium channel blocker is nimodipine administered at a dosage of 60 mg. every 4 hours.

31. The method of claim 27 wherein said calcium channel blocker is felodipine administered orally in quantities between 2.5 and 20 mg.

32. The method of claim 31 wherein said felodipine is administered orally in a dosage of approximately 15 mg.

33. The method of claim 27 wherein the said administration is continued from the first diagnosis of Bell's Palsy or Ramsay Hunt up to the tenth day after first symptoms.

34. The method of claim 32, wherein said dosage of felodipine is administered daily for a 10 day period.

35. The method of claim 32, wherein said felodipine is administered as nifedipine in approximately 3 daily doses in the range of 10–20 mg.

36. The method of claim 32, wherein said felodipine is administered as nifedipine in approximately a daily dose in the range of 30–60 mg.

37. The method of claim 32, wherein said felodipine is administered as nifedipine in approximately a daily dose of 30 mg.

38. The method of claim 31, wherein acyclovir or other herpes viral antagonist such as famciclovir is also administered in therapeutically effective dosages.

39. The method of claim 38 wherein said acyclovir is administered in dosages of approximately 400 mg.

40. The method of claim 38 wherein said acyclovir is administered approximately 5 times daily for an approximately 10 day period.

41. The method of claim 39, wherein said acyclovir is administered approximately 5 times daily for an approximately 10 day period.

42. The method of claim 3, wherein said felodipine is adminstered as immediate release nifedipine three times daily in dosages of 10–20 mg.

43. The method of claim 3, wherein said felodipine is administered as immediate release nifedipine in a dose of 10 mg three times daily.

44. The method of claim 16 wherein said felodipine is administered as immediate release nifedipine three times daily in dosages of 10–20 mg.

45. The method of claim 16 wherein said felodipine is administered as immediate release nifedipine in approximately a dose of 10 mg three times daily.

46. The method of claim 32, wherein said felodipine is administered as immediate release nifedipine three times daily in dosages of 10–20 mg.

47. The method of claim 32, wherein said felodipine is administered as immediate release nifedipine three times daily in dosages of 10 mg.

* * * * *